United States Patent [19]
Barnard

[11] Patent Number: 4,705,514
[45] Date of Patent: Nov. 10, 1987

[54] ABSORBENT DENTAL ROLL

[75] Inventor: Ralph G. Barnard, Gastonia, N.C.

[73] Assignee: Barnhardt Manufacturing Corporation, Charlotte, N.C.

[21] Appl. No.: 821,073

[22] Filed: Jan. 22, 1986

[51] Int. Cl.$^4$ ............................................. A61F 13/20
[52] U.S. Cl. ........................................ 604/383; 604/1; 604/358; 604/904; 604/384; 604/370; 433/136; 433/139
[58] Field of Search ............... 604/366, 370, 374, 375, 604/377, 378, 383, 379, 904, 358, 384; 433/136–139

[56] References Cited

U.S. PATENT DOCUMENTS

| | | |
|---|---|---|
| 271,625 | 2/1883 | Goff .................................... 604/904 |
| 1,652,108 | 12/1927 | Forbis .................................... 604/1 |
| 1,812,655 | 6/1931 | Ladd . | |
| 1,985,667 | 12/1934 | Nelson et al. . | |
| 2,437,265 | 3/1948 | Manning ............................ 604/904 |
| 2,608,901 | 9/1952 | Goldman . | |
| 2,705,498 | 4/1955 | Johnson .............................. 604/379 |
| 3,523,535 | 8/1970 | Croon et al. ........................ 604/904 |
| 4,335,721 | 6/1982 | Matthews ............................ 604/904 |

OTHER PUBLICATIONS

Dental Survey, "Johnson & Johnson", Jun., 1934, entitled: CEL-U-ROL.
Dental Survey, "Richmond Dental Cotton Co.", Nov., 1979, entitled: Soft-Crossed Rolls.

Primary Examiner—C. Fred Rosenbaum
Assistant Examiner—Sherri E. Vinyard
Attorney, Agent, or Firm—Bell, Seltzer, Park & Gibson

[57] ABSTRACT

A dental roll having a wrapper or covering of nonwoven fibers surrounding an absorbent body of cellulosic fibers and wherein the wrapper is constructed to have greater stretchability radially of the absorbent body than lengthwise thereof so as to resiliently maintain the body in compacted, dense condition while permitting the dental rolls to readily conform to the contour of the mouth and lip of the patient.

9 Claims, 5 Drawing Figures

ABSORBENT DENTAL ROLL

BACKGROUND OF THE INVENTION

This invention relates to absorbent rolls for a variety of purposes such as dental rolls and the like. As is well-known, dental rolls are used by dentists in patients' mouths for absorbing moisture and saliva. Also, dental rolls are used by dentists as spacers, i.e., to space a patient's cheek away from the tooth work area.

The principal object of this invention is to provide an absorbent roll such as a dental roll which lends itself for high speed and more economical production thereof. Further, the new dental roll is constructed so as to be as comfortable in the mouth of the patient as dental rolls presently being made by applicant's assignee. These prior art dental rolls are made in accordance with Goldman U.S. Pat. No. 2,608,901, commonly owned by applicant's assignee and which dental rolls are characterized by having relatively open braided coverings and have been widely accepted by dentists as the ultimate and top of the line in dental rolls.

A more specific object of this invention is to provide a dental roll having a covering of nonwoven fibers surrounding an absorbent body of cellulosic fibers and wherein the covering is so constructed as to have greater stretchability radially of the absorbent body than lengthwise thereof so as to resiliently maintain the body in compacted dense condition while permitting the dental rolls to readily conform to the contour of the mouth and lip of the patient, and to facilitate a dentist splitting the covering longitudinally for the purpose of expanding and exposing the body of cellulosic fibers and gaining access to bunches of the body fibers for use as small swabs or the like.

Further objects, features and advantages of this invention will be apparent in connection with the following description of the invention as exemplified in connection with the accompanying drawings wherein.

Figures 1, 2:
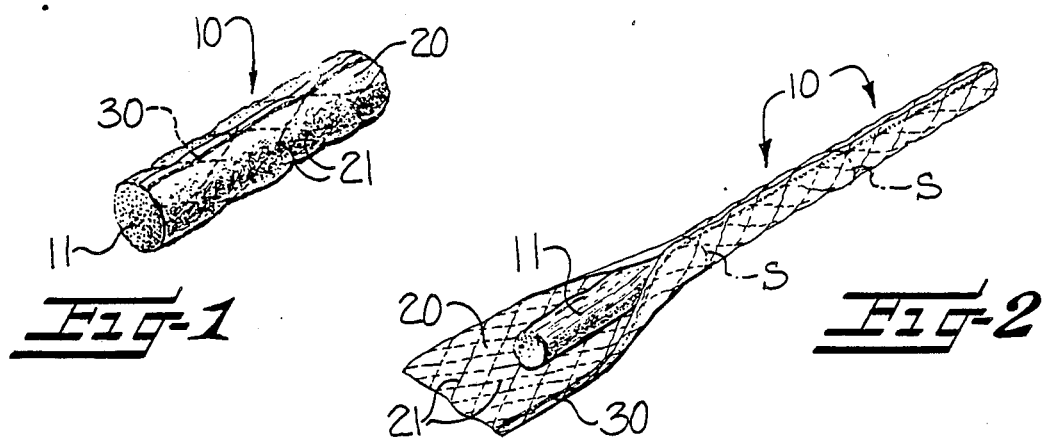
FIG. 1 is a perspective view of the absorbent dental roll product.
FIG. 2 is a schematic perspective view illustrating a rod being formed and containing a series of dental rolls prior to the dental rolls being severed into individual units.

Referring now specifically to the drawings, reference numeral 10 broadly indicates the dental roll of this invention which comprises two main components, i.e., a cylindrical resilient body 11, and a wrapper or covering 20 therearound. As schematically illustrated in FIG. 2, the dental roll of this invention may be readily formed in the manner of long rods which may be suitably severed apart as at S to form the individual units 10 of the dental roll.

The body 11 of the dental roll is formed of a fibrous resilient material and preferably of highly absorbent cellulosic fibers and more particularly, bleached cotton fibers for enchancing the absorbency and appearance thereof. The fibers of the resilient body 11 are formed as a web of substantially parallel fibers which have subsequently been gathered and consolidated into the cylindrical form as illustrated in the drawings.

Figure 5:
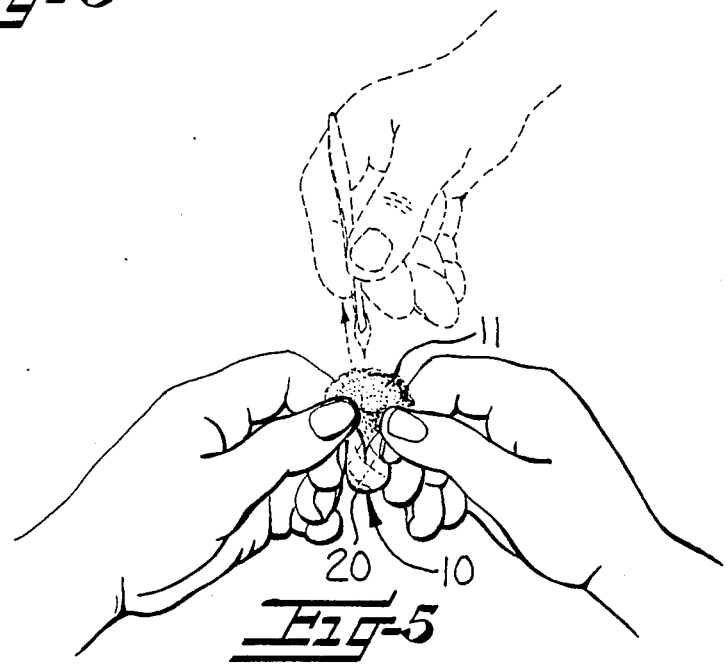
FIG. 5 is a schematic view illustrating the ease of rupturing of the dental rolls if desired by the dentist to expose cotton body fibers for use as bunches for a swab.

The wrapper or covering 20 for the dental roll is formed of a nonwoven fibrous material preferably of cellulosic fibers for enhanced moisture absorbency thereof. Other types of fibers may be used if moisture absorbency is not of that importance. The nonwoven fibrous sheet 20 is so arranged around the body 11 of the dental roll as to position the fibers forming the wrapper longitudinally of the dental roll. In this regard, it has been determined that where the fibrous sheet is formed of cellulosic fibers of the type of viscose rayon fibers spunbonded together, that the orientation of the fibers in the sheet is predominately lengthwise of the sheet so as to substantially stabilize the lengthwise dimension of the sheet for facilitating machine handling thereof in the formation of the dental roll. Furthermore, it has been determined that this type of covering or wrapper facilitates the lengthwise tearing thereof and the rupturing of the dental roll, if desired by the dentist, so as to expand and expose the cotton body fibers when using the dental roll as a source for bunches of cotton fibers to be used as a swab. This is schematically illustrated in FIG. 5.

Figures 3, 4:
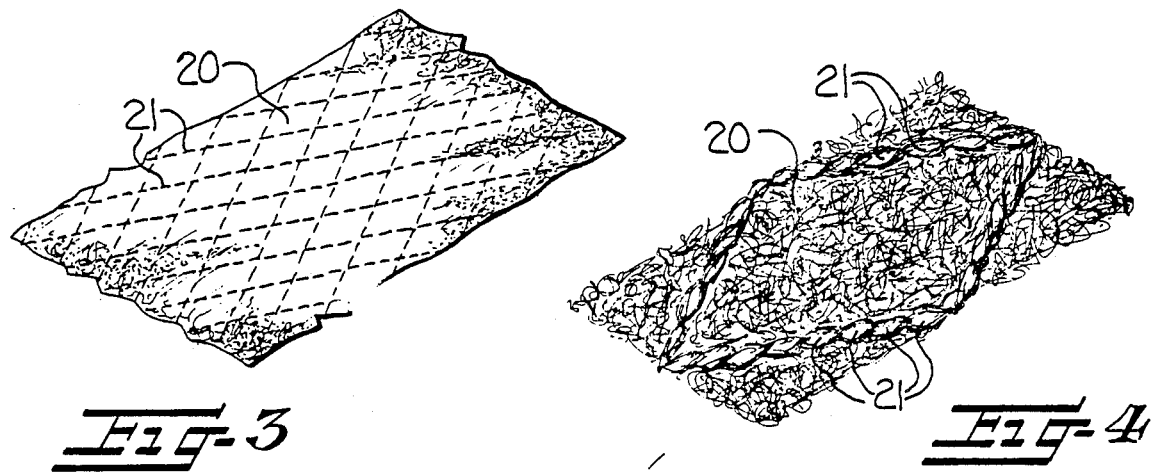
FIG. 3 is a fragmentary perspective view of the nonwoven covering or wrapper material for the dental roll.
FIG. 4 is a greatly enlarged fragmentary view of the wrapper material of FIG. 3 and illustrating the diamond pattern arrangement of the perforated openings therein.

Further, it has been determined that desirably the non-woven sheet material 20 should have perforations 21 therein, for facilitating the flow of moisture into the body 11 of the dental roll. Furthermore, when the perforations are arranged in a diamond pattern, as illustrated in FIGS. 3 and 4, it has been determined that the dental roll presents the appearance of a braided wrapper of interlaced textile yarns. This is deemed to be desirable, as indicated earlier, since dentists have accepted the braided wrapper type of dental roll for many years.

For maintaining the wrapper 20 in surrounding condition to the body 11 of the dental roll, a linearly arranged line of adhesive 30, preferably in the form of a hot melt adhesive is provided. As illustrated in FIGS. 1 and 2, this adhesive 30 is provided on the inner surface of the outer overlapping portion so that the line of adhesive 30 is desirably not visible. Furthermore, the adhesive 30 thusly interposed between the overlapping portions of the sheet material would not be found objectionable to the sensitive areas of a patient's mouth.

It has been determined that the wrapper 20 for the dental roll should be formed from a nonwoven fibrous sheet that is relatively thin and translucent and of a weight of no more than about 50 grams per square meter. Further, as earlier indicated, the fibrous sheet should have greater stretchability widthwise than lengthwise thereof so as to resiliently maintain the body in compacted, dense condition and to readily conform to contours of the mouth and lip of a patient.

In the drawings and specification there has been set forth a preferred embodiment of the invention, and although specific terms are employed, they are used in a generic and descriptive sense only and not for purposes of limitation.

That which is claimed is:

1. An absorbent readily rupturable dental roll comprising an elongate cylindrical resilient body of predetermined length formed of highly absorbent cellulosic fibers in compact dense condition, an open-ended tubular wrapper surrounding and covering said resilient body and holding the body of cellulosic fobers in the compact dense condition, said wrapper being formed of readily rupturable material for facilitating lengthwise tearing of the sheet and rupturing of the dental roll, if desired by the dentist, to expand and expose the highly absorbent fibers of the body when using the dental roll as a source for bunches of fibers to be used as a swab, said wrapper comprising a nonwoven elongate fibrous sheet of cellulosic fibers for enhanced moisture absorbency of the dental roll, said elongate fibrous sheet having greater stretchability widthwise than lengthwise thereof and also having linearly arranged overlapping longitudinal edges, and adhesive means extending along said longitudinal edges and securing the fibrous sheet in tubular form so as to form a radially resilient tube for resiliently maintaining said body of cellulosic fibers in the wrapper in compact dense condition and to conform to the contour of the mouth and lip of the patient.

2. A dental roll according to claim 1, wherein said cellulosic fibers of said body are bleached cotton fibers, and wherein said elongate fibrous sheet of cellulosic fibers is formed of viscose rayon fibers spun bonded together to form the sheet, and wherein the orientation of the fibers in the sheet is predominately lengthwise of the sheet to substantially stabilize the lengthwise dimension of the sheet for facilitating machine handling thereof in the formation of the dental roll and for facilitating lengthwise tearing of the sheet and rupturing of the dental roll, if desired by the dentist.

3. A dental roll according to claim 1, wherein said sheet of cellulosic fibers has perforations therein for facilitating the flow of moisture into the body of the dental roll.

4. A dental roll according to claim 1, wherein said sheet of cellulosic fibers has a diamond pattern formed of small perforations therein serving to facilitate the flow of moisture into the body of the dental roll and presenting the appearance of a braided wrapper of interlaced textile yarns.

5. A dental roll according to claim 1, wherein said fibrous sheet is of a weight of no more than about 50 grams per square meter and said adhesive means securing the fibrous sheet in tubular form is a hot melt adhesive.

6. An absorbent readily rupturable dental roll comprising an elongate cylindrical resilient body of predetermined length formed of highly absorbent bleaching cotton fibers in compact dense condition, an open-ended tubular wrapper surrounding and covering said resilient body and holding the body of cotton fibers in the compact dense condition, said wrapper being formed of readily rupturable material for facilitating lengthwise tearing of the sheet and rupturing of the dental roll, if desired by the dentist, to expand and expose the highly absorbent fibers of the body when using the dental roll as a source for bunches of fibers to be used as a swab, said wrapper comprising a nonwoven elongate fibrous sheet of cellulosic fibers for enhanced moisture absorbency of the dental roll, said elongate fibrous sheet being relatively thin and translucent and of a weight of no more than about 50 grams per square meter and having greater stretchability widthwise than lengthwise thereof and also having linearly arranged overlapping longitudinal edges, and hot melt adhesive extending along said longitudinal edges and securing the fibrous sheet in tubular form so as to form a radially resilient tube for resiliently maintaining said body of cotton fibers in the wrapper in compact dense condition.

7. A dental roll according to claim 6, wherein said elongate fibrous sheet of cellulosic fibers is formed of viscose rayon fibers spun bonded together to form the sheet, and wherein the orientation of the fibers in the sheet is predominately lengthwise of the sheet to substantially stabilize the lengthwise dimension of the sheet for facilitating machine handling thereof in the formation of the dental roll and for facilitating lengthwise tearing of the sheet and rupturing of the dental roll, if desired by the dentist.

8. A dental roll according to claim 9, wherein said sheet of cellulosic fibers has perforations therein for facilitating the flow of moisture into the body of the dental roll.

9. A dental roll according to claim 9, wherein said sheet of cellulosic fibers has a diamond pattern formed of small perforations therein serving to facilitate the flow of moisture into the body of the dental roll and also presenting the appearance of a braided wrapper of interlaced textile yarns.

* * * * *

UNITED STATES PATENT AND TRADEMARK OFFICE
CERTIFICATE OF CORRECTION

PATENT NO. : 4,705,514

DATED : November 10, 1987

INVENTOR(S) : Ralph G. Barnard

It is certified that error appears in the above-identified patent and that said Letters Patent is hereby corrected as shown below:

Column 2, line 66, delete "fobers" and insert --fibers--

Column 4, line 34, delete "claim 9" and insert --claim 6--

Column 4, line 38, delete "claim 9" and insert --claim 6--

Signed and Sealed this

Nineteenth Day of April, 1988

Attest:

DONALD J. QUIGG

*Attesting Officer*      *Commissioner of Patents and Trademarks*